United States Patent
Hashimoto et al.

(10) Patent No.: US 10,835,333 B2
(45) Date of Patent: Nov. 17, 2020

(54) REMOTE CONTROL ROBOT SYSTEM

(71) Applicant: KAWASAKI JUKOGYO KABUSHIKI KAISHA, Kobe (JP)

(72) Inventors: Yasuhiko Hashimoto, Kobe (JP); Masayuki Kamon, Akashi (JP)

(73) Assignee: KAWASAKI JUKOGYO KABUSHIKI KAISHA, Kobe (JP)

(*) Notice: Subject to any disclaimer, the term of this patent is extended or adjusted under 35 U.S.C. 154(b) by 294 days.

(21) Appl. No.: 15/755,102

(22) PCT Filed: May 27, 2016

(86) PCT No.: PCT/JP2016/002596
§ 371 (c)(1),
(2) Date: Feb. 26, 2018

(87) PCT Pub. No.: WO2017/033366
PCT Pub. Date: Mar. 2, 2017

(65) Prior Publication Data
US 2018/0243921 A1 Aug. 30, 2018

(30) Foreign Application Priority Data
Aug. 25, 2015 (JP) .................. 2015-165479

(51) Int. Cl.
A61B 34/30 (2016.01)
A61B 34/37 (2016.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
USPC .................................. 700/245–264
See application file for complete search history.

(56) References Cited

U.S. PATENT DOCUMENTS 5,652,849 A * 7/1997 Conway ................ G08B 25/14
348/115
9,582,080 B1 * 2/2017 Tilton ..................... G10L 15/02
(Continued)

FOREIGN PATENT DOCUMENTS

CN 104827457 A 8/2015
JP S61-61191 U 4/1986
(Continued)

OTHER PUBLICATIONS

Feb. 27, 2018 International Preliminary Report on Patentability issued in Patent Application No. PCT/JP2016/002596.
(Continued)

Primary Examiner — Jonathan L Sample
(74) Attorney, Agent, or Firm — Oliff PLC

(57) ABSTRACT

Robot main body having robotic arm, remote control device including robotic arm operational instruction input part for operator to control by touching, to input operational instruction for robotic arm, and contactless action detecting part configured to detect contactless action including at least one given operation instructing action of operator, and control device communicably connected to remote control device and configured to control operation of robot main body, are provided. Control device includes memory part configured to store operational instruction content data defining an operation mode of robot main body corresponding to at least one operation instructing action, operational instruction content identifying module to identify operation mode of robot main body of the operation instructing action detected by contactless action detecting part based on operational instruction content data, and motion controlling module
(Continued)

configured to control operation of robot main body based on operation mode identified by operational instruction content identifying module.

6 Claims, 9 Drawing Sheets

(51) Int. Cl.
| | |
|---|---|
| G05B 19/418 | (2006.01) |
| B25J 9/00 | (2006.01) |
| B23P 19/04 | (2006.01) |
| B25J 13/00 | (2006.01) |
| B25J 19/04 | (2006.01) |
| B25J 9/16 | (2006.01) |
| B25J 13/08 | (2006.01) |
| B25J 3/00 | (2006.01) |
| B25J 13/06 | (2006.01) |
| B25J 18/00 | (2006.01) |
| B25J 19/02 | (2006.01) |
| B25J 3/04 | (2006.01) |
| B23Q 15/12 | (2006.01) |
| B25J 13/02 | (2006.01) |
| B25J 11/00 | (2006.01) |
| G06F 3/01 | (2006.01) |
| H04N 5/232 | (2006.01) |
| H04N 7/18 | (2006.01) |
| A61B 34/32 | (2016.01) |
| G06T 7/62 | (2017.01) |
| G06T 7/70 | (2017.01) |
| B23P 21/00 | (2006.01) |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(56) References Cited

U.S. PATENT DOCUMENTS

| | | | |
|---|---|---|---|
| 10,406,686 B2* | 9/2019 | Boca | B25J 9/1656 |
| 2002/0181773 A1* | 12/2002 | Higaki | G06F 3/017 |
| | | | 382/190 |
| 2013/0211592 A1* | 8/2013 | Kim | G06F 3/017 |
| | | | 700/258 |
| 2015/0032258 A1* | 1/2015 | Passot | G06N 3/008 |
| | | | 700/250 |
| 2015/0217449 A1* | 8/2015 | Meier | B25J 9/1602 |
| | | | 700/257 |
| 2015/0217450 A1* | 8/2015 | Huang | B25J 9/1671 |
| | | | 700/259 |
| 2015/0339826 A1* | 11/2015 | Buibas | G06K 9/00355 |
| | | | 382/106 |
| 2016/0046023 A1* | 2/2016 | Nagendran | B25J 9/1689 |
| | | | 700/248 |
| 2016/0350589 A1* | 12/2016 | Chiu | B25J 13/00 |

FOREIGN PATENT DOCUMENTS

| | | |
|---|---|---|
| JP | 2003-311661 A | 11/2003 |
| JP | 2013-510672 A | 3/2013 |
| JP | 2014-104527 A | 6/2014 |

OTHER PUBLICATIONS

Aug. 9, 2016 International Search Report issued in Patent Application No. PCT/JP2016/002596.

May 5, 2017 Taiwanese Office Action and Search Report issued in Taiwan Patent Application No. 105126689.

* cited by examiner

| ATTITUDE OF RESPECTIVE FINGERS, HAND MOTION | 1ST HAND GESTURE | 2ND HAND GESTURE | 3RD HAND GESTURE | 4TH HAND GESTURE | 5TH HAND GESTURE |
|---|---|---|---|---|---|
| INSTRUCTION CONTENT | HOLD WORKPIECE | REFERENCE ATTITUDE | ADVANCE | RELEASE WORKPIECE | RETREAT |

FIG. 4

| SOUND CONTENT | 1ST SOUND | 2ND SOUND | 3RD SOUND | 4TH SOUND | 5TH SOUND |
|---|---|---|---|---|---|
| | "HOLD WORKPIECE" | "TAKE REFERENCE ATTITUDE" | "ADVANCE" | "RELEASE WORKPIECE" | "RETREAT" |
| INSTRUCTION CONTENT | HOLD WORKPIECE | REFERENCE ATTITUDE | ADVANCE | RELEASE WORKPIECE | RETREAT |

FIG. 6

REMOTE CONTROL ROBOT SYSTEM

TECHNICAL FIELD

The present disclosure relates to a remote control robot system.

BACKGROUND ART

Conventionally, systems including a remote operation control device which causes a robot to perform a necessary work are known (e.g., see Patent Document 1).

The remote operation control device of this system is a remote operation control device which causes the robot to perform the necessary work while remotely controlling, by an operation control system, operation of the robot which is installed in a work environment. The remote operation control device includes an operational instruction generating means for generating an operational instruction for automated operation of the robot, and a manipulating means by which the robot is manually operated. The robot is switched from the automated operation to the manual operation in response to an instruction to switch to the manual operation. Thus, for a work which is difficult to be automated, it may be switched to the manual operation to perform the work.

REFERENCE DOCUMENT OF CONVENTIONAL ART

Patent Document

[Patent Document 1] JP2003-311661A

DESCRIPTION OF THE DISCLOSURE

Problems to be Solved by the Disclosure

Meanwhile, for example, when attempting to manually operate a self-running robot provided with a master-slave type slave arm, there has been a problem that a means for inputting a traveling operation instruction is required in addition to a master arm which inputs an operational instruction for the slave arm, resulted in the configuration of the manipulating means being complex. Such problem is not for the self-running robot alone but is a common problem when it is necessary to give an operational instruction other than the operational instruction for the slave arm to the robot. Further, with the configuration of the manipulating means being complex, there has been a problem that a required education period for an operator to be familiar with the method of controlling the manipulating means becomes longer.

SUMMARY OF THE DISCLOSURE

In order to solve the above problem, a remote control robot system according to one aspect of the present disclosure includes a robot main body having a robotic arm, a remote control device including a robotic arm operational instruction input part for an operator to control by touching, to input an operational instruction for the robotic arm, and a contactless action detecting part configured to detect a contactless action including at least one given operation instructing action of the operator, and a control device communicably connected to the remote control device and configured to control operation of the robot main body. The control device includes a memory part configured to store operational instruction content data defining an operation mode of the robot main body corresponding to the at least one operation instructing action, an operational instruction content identifying module configured to identify the operation mode of the robot main body corresponding to one of the operation instructing action detected by the contactless action detecting part based on the operational instruction content data, and a motion controlling module configured to control operation of the robot main body based on the operation mode identified by the operational instruction content identifying module.

With this configuration, an action matching an impression on the operational instruction can be set as the operation instructing action, and a required education period for the operator to be familiar with the method of manipulating the remote control robot system can be shortened.

Further, since it is possible to input the operational instruction to the contactless action detecting part without touching, there is no need to visually recognize the contactless action detecting part at the time of inputting an operational instruction to the contactless action detecting part, and it is possible to promptly input the operational instruction to the contactless action detecting part.

Furthermore, it is possible that actions which are clearly distinguishable from each other as the respective operation instructing actions are selected and set as the operation instructing actions, preventing incorrect input and erroneous recognition by the operator.

The operation instructing action may be an operator's hand gesture.

With this configuration, the operator can input the operational instruction by his/her hand gesture.

The hand gesture may be inputted by one of operator's hands.

With this configuration, it is possible to make a hand gesture with one hand to input the operational instruction for the robot main body to the remote control robot system, while simultaneously controlling the robotic arm operational instruction input part with the other hand to input the operational instruction for the robotic arm to the remote control robot system.

The operation instructing action may be operator's sound of voice.

With this configuration, the operational instruction can be inputted to the remote control robot system by the operator's sound of voice.

The robotic arm may have an arm that is attachable, at its tip-end part, of an end effector configured to handle a workpiece, and that is configured to move the end effector within a given operational area by moving the tip-end part with respect to a base-end part. The operation mode of the robot main body in the operational instruction content data may include an operation mode in which the end effector is operated.

With this configuration, the operational instruction for the robotic arm can be inputted to the remote control robot system by the operation instructing action.

The robot main body may include a traveling unit configured to cause the robot main body to travel. The operation mode of the robot main body defined by the operational instruction content data may include an operation mode in which the robot main body travels by the traveling unit.

With this configuration, a traveling instruction for the traveling unit can be inputted to the remote control robot system by the operation instructing action.

Effect of the Disclosure

The present disclosure has an effect that the required education period for the operator to be familiar with the method of manipulating the remote control robot system can be shortened.

BRIEF DESCRIPTION OF DRAWINGS

FIG. 4 is a view illustrating a configuration example of operational instruction content data stored in a memory part of the remote control robot system in FIG. 1.

FIG. 6 is a view illustrating a configuration example of operational instruction content data according to a second embodiment of the present disclosure.

MODES FOR CARRYING OUT THE DISCLOSURE

Figure 1:
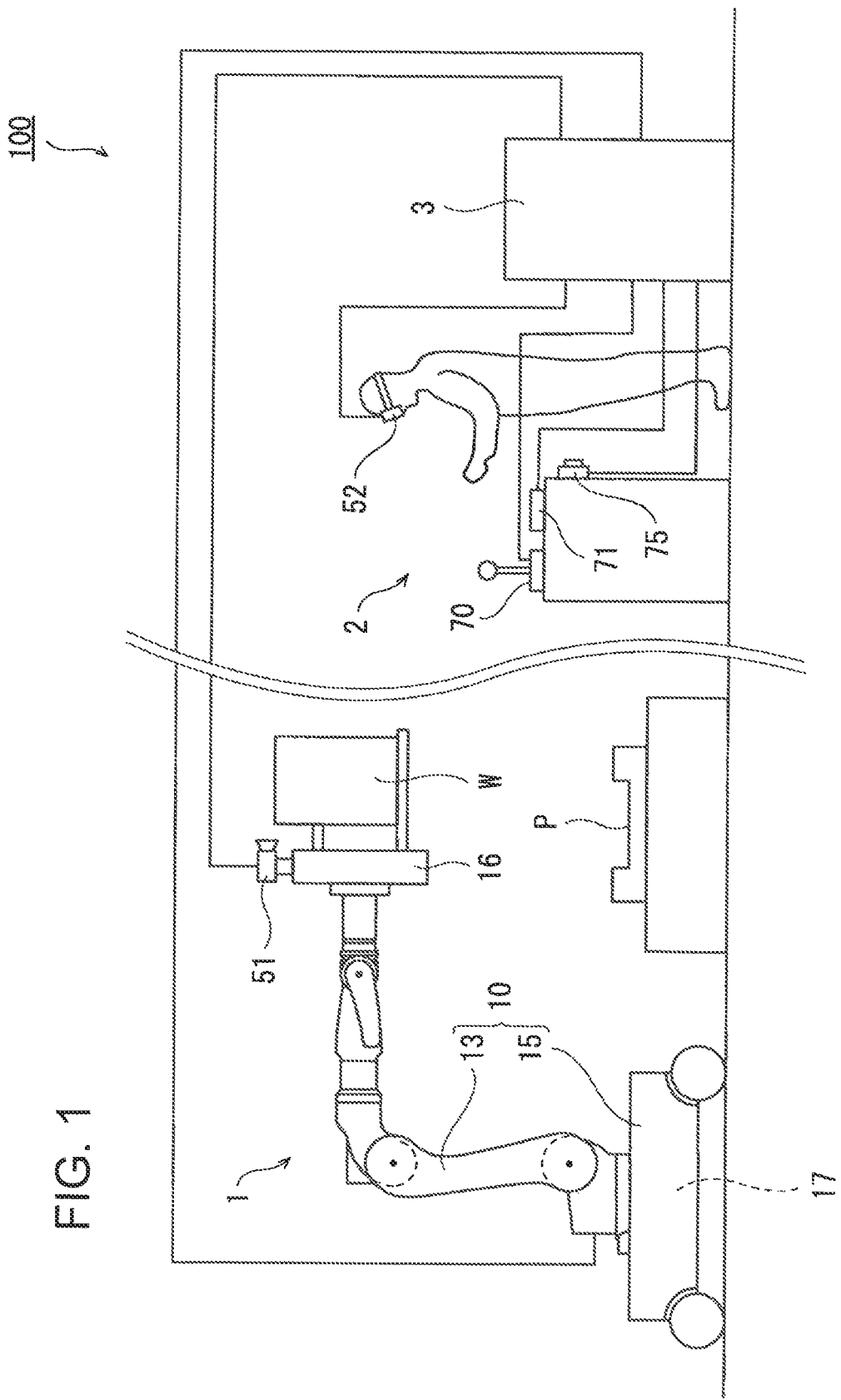
FIG. 1 is a view schematically illustrating a configuration example of a remote control robot system according to a first embodiment of the present disclosure.

Hereinafter, embodiments of the present disclosure will be described with reference to the accompanying drawings. Note that the present disclosure is not to be limited by these embodiments. Further, below, the same reference characters are assigned to the same or corresponding components throughout the figures and redundant description is omitted.

First Embodiment

FIG. 1 is a view schematically illustrating a configuration example of a remote control robot system 100 according to the first embodiment of the present disclosure.

As illustrated in FIG. 1, the remote control robot system 100 includes a robot main body 1, a remote control device 2, and a control device 3.

The remote control robot system 100 according to this embodiment is a system including a master-slave type robot in which a slave arm operates following a motion of a master arm. The remote control robot system 100 is configured so that an operator located at a position distant from a working area (outside the working area) of a slave arm 10 (a robotic arm, will be described later in detail) of the robot main body 1 can input an operational instruction to the remote control robot system 100 by moving a master arm 70 of the remote control device 2 (a robotic arm operational instruction input part, will be described later in detail), to make the slave arm 10 perform an operation corresponding to the operational instruction by a control of the control device 3 to perform a specific work, such as an assembling work of components. The slave arm 10 of the remote control robot system 100 is also configured so that the slave arm 10 may automatically perform a given operation by a control of the control device 3 without the operator's control of the master arm 70.

Configuration Example of Robot Main Body

The robot main body 1 includes the slave arm 10, an end effector 16, a traveling unit 17, and a camera 51, and is installed in the working area.

The slave arm 10 is, for example, an arm of an articulated-type industrial robot, but it is not limited to this. The slave arm 10 includes an arm main body 13 and a pedestal 15.

The arm main body 13 includes a plurality of links sequentially connected in a direction from a base-end part toward a tip-end part, and one or more joints coupling the adjacent links so that one of them is rotatable with respect to the other link. Further, the end effector 16 is coupled to the tip-end part of the arm main body 13. Moreover, the arm main body 13 is configured so that the tip-end part is moved with respect to the base-end part by rotating the joint, and the end effector 16 thus moves within a given operational area. The arm main body 13 includes a robotic arm drive part (not illustrated) which drives a plurality of joint axes. Further, the pedestal 15 supports the arm main body 13 and the end effector 16.

In this embodiment, the end effector 16 is configured to be capable of performing a holding operation for holding a workpiece and a releasing operation for releasing the held workpiece, and is attached to the tip-end part of the arm main body 13 via a wrist joint. The end effector 16 includes an end effector drive part (not illustrated) for performing the holding operation and the releasing operation. In this embodiment, although the end effector 16 is configured to be capable of performing the holding operation and the releasing operation so that, for example, the assembling work of the components can be performed, it is not limited to this. Alternatively to this, it may be configured so that, for example, a welding work and a paint work can be performed.

The traveling unit 17 is provided to the pedestal 15 and causes the entire robot main body 1 to travel. The traveling unit 17 has, for example, wheels and a wheel drive part (not illustrated) which rotatably drives the wheels. The wheel drive part rotatably drives the wheels to move the robot main body 1. Thus, in this embodiment, the robot main body 1 is a self-running robot which is self-runnable, but it is not limited to this.

The camera 51 is a camera which images operation statuses of the slave arm 10 and the end effector 16. In this embodiment, the camera 51 is attached to the end effector 16, but it is not limited to this. Alternatively to this, it may be attached to the tip-end part of the slave arm 10e or the pedestal 15. Further, it may be fixed at a given position in the working area.

Configuration Example of Remote Control Device

The remote control device 2 is installed outside the working area, is communicably connected to the control device, and controls the operation of the robot main body 1.

The remote control device 2 includes the master arm 70, a contactless action detecting part 71, a mode selecting part 75, and a monitor 52.

The master arm 70 is a device for the operator to control by touching to input an operational instruction for the slave arm 10 from the operator. In this embodiment, the master arm 70 is a device by which a target attitude of the slave arm 10 can be inputted and an operation mode for the slave arm 10 can be inputted.

Figure 2:
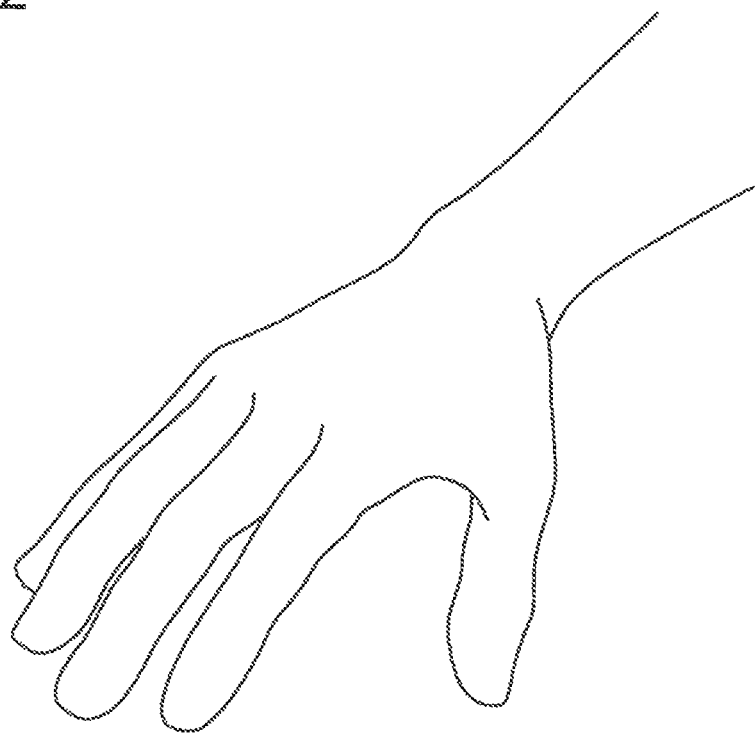
FIG. 2 is a perspective view illustrating a configuration example of a contactless action detecting part of the remote control robot system in FIG. 1.
Figure 2:
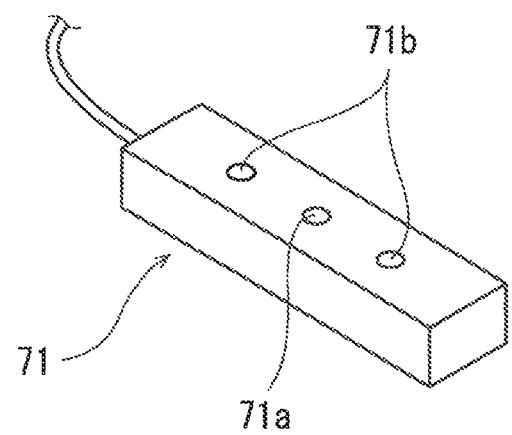

FIG. 2 is a perspective view illustrating a configuration example of the contactless action detecting part 71.

The contactless action detecting part 71 detects a contactless action which includes one or more operation instructing actions of the operator within a given detection range. The contactless action refers to actions related to body gestures, hand gestures, and vocalizations of the operator, and does not include actions of touching an input device to control it. The contactless action includes, for example, the operator making a hand gesture, the operator speaking, the operator exhaling, the operator changing his/her posture, the operator shaking his/her neck up-and-down or to the sides, the operator tilting the neck, the operator blinking, the operator gazing at a given place, the operator changing his/her facial expression, the operator stomping, and the operator chewing.

In this embodiment, the given operation instructing action is the operator making the hand gesture, and the contactless action detecting part 71 is a detector which detects the operator's hand gesture within a range set above the contactless action detecting part 71. As illustrated in FIG. 2, the contactless action detecting part 71 includes an infrared radiator 71a for radiating an infrared ray upwardly and a stereo camera 71b for receiving the infrared ray radiated from the infrared radiator 71a and reflected on a target object. It is further configured to calculate an attitude of each finger (a shape of a hand) and a motion of the hand based on an image captured by the stereo camera 71b. Further, the contactless action detecting part 71 is installed near the master arm 70 and configured to be capable of manipulating the robot main body 1 while parallelly performing an input of the operational instruction to the master arm 70 and an input of the operational instruction to the contactless action detecting part 71. For example, LEAP (®) of Leap Motion Inc. may be used as the contactless action detecting part 71.

The mode selecting part 75 is an input part for the operator to input a selecting instruction of a working mode in which the slave arm 10 is operated, and it is possible to input the selecting instruction of one working mode from an automatic mode, a correctable automatic mode, and a manual mode which are described later.

The monitor 52 is a monitor for the operator to confirm a work situation of the slave arm 10. The monitor 52 is installed in a space where the master arm 70 is provided. Further, in this embodiment, the monitor 52 is, for example, a head mounted display which may be attached to the operator's head, but it is not limited to this.

Configuration Example of Control Device

Figure 3:
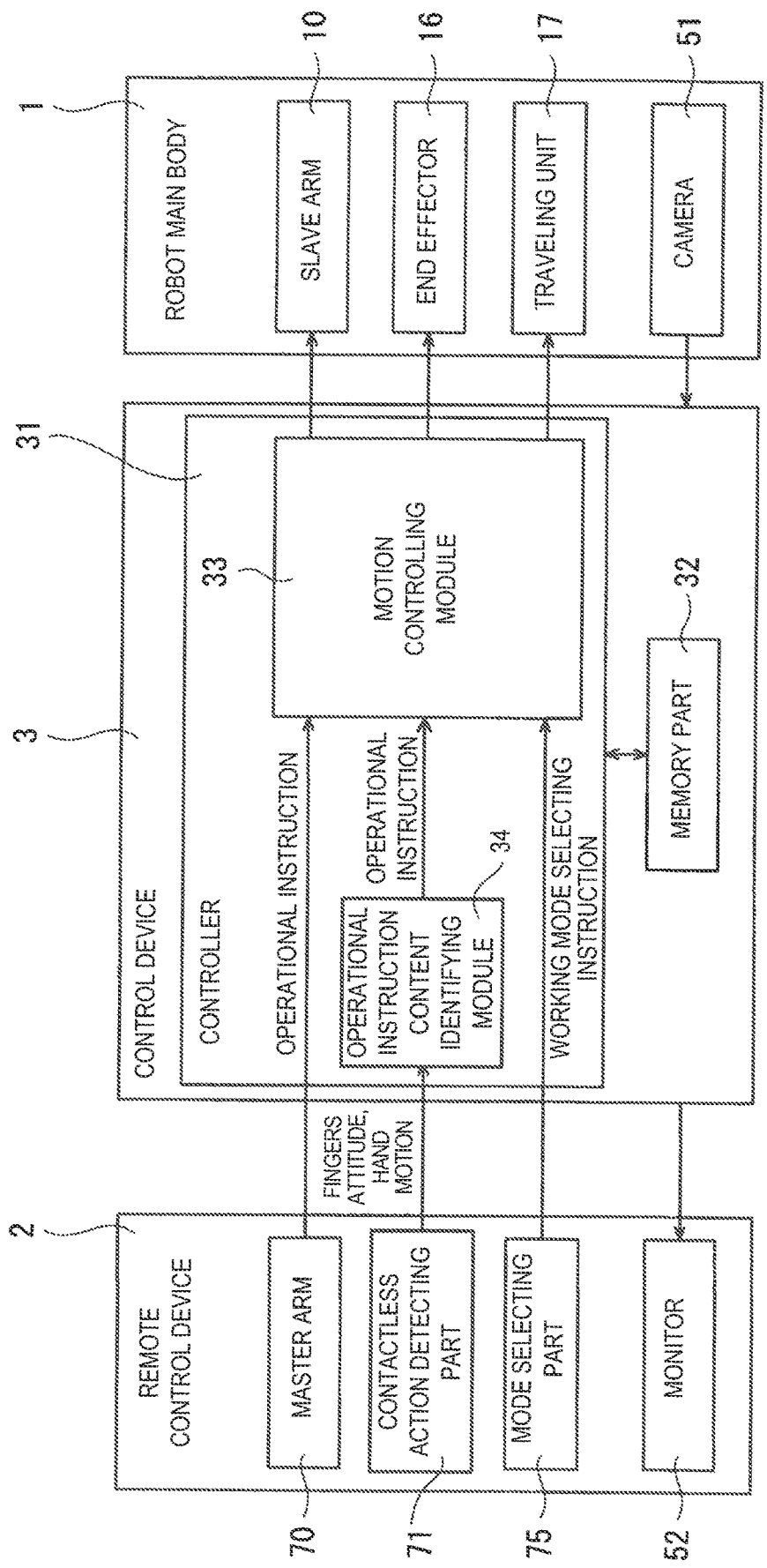
FIG. 3 is a block diagram schematically illustrating a configuration example of a control system of the remote control robot system in FIG. 1.

FIG. 3 is a block diagram schematically illustrating a configuration example of a control system of the remote control robot system 100.

The control device 3 is communicably connected to the remote control device 2 and controls the operation of the robot main body 1.

As illustrated in FIG. 3, the control device 3 includes a controller 31 and a memory part 32. The control device 3 may be comprised of a single controller which performs a central control or a plurality of controllers which perform distributed controls.

The controller 31 is, for example, comprised of a microcontroller, a CPU, an MPU, a logic circuit, a PLC, etc.

The controller 31 includes a motion controlling module 33 and an operational instruction content identifying module 34. The motion controlling module 33 and the operational instruction content identifying module 34 are functional blocks implemented by an arithmetic unit executing a given control program stored in the memory part 32.

The motion controlling module 33 controls the operation of the robot main body 1, including the operation of the slave arm 10, the operation of the end effector 16, and the operation of the traveling unit 17. The controls of the operation of the end effector 16 and the operation of the traveling unit 17 are performed, for example, by controlling a current supplied to each drive part.

The motion controlling module 33 is configured to control the slave arm 10 according to one mode selected from the manual mode, the automatic mode, and the correctable automatic mode by the mode selecting part 75.

The manual mode is a working mode in which the control device 3 operates the robot main body 1 according to the operational instruction inputted to the remote control robot system 100 via the master arm 70 or the contactless action detecting part 71. That is, in the manual mode, the motion controlling module 33 operates the slave arm 10 based on the operational instruction inputted to the master arm 70, and further controls the operation of the robot main body 1 based on an operation mode identified by the operational instruction content identifying module 34 described later. This manual mode includes a mode in which, when the control device 3 operates the robot main body 1 based on the operational instruction inputted by the operator to the master arm 70 or the contactless action detecting part 71, the control device 3 applies a correction in a part of the operational instruction inputted by the operator to operate the robot main body 1.

The automatic mode is a working mode in which the control device 3 operates the robot main body 1 according to a preset operation mode stored in the memory part 32. Note that, it is configured such that in the state where the automatic mode is selected, even if the operator inputs an operational instruction by controlling the master arm 70 or the contactless action detecting part 71, the control device 3 does not reflect the inputted operational instruction to the operation mode of the robot main body 1.

The correctable automatic mode is a working mode in which, when the operator inputs the operational instruction by controlling the master arm 70 or the contactless action detecting part 71 in a state where the control device 3 is operating the robot main body 1 according to the preset operation mode stored in the memory part 32, the control device 3 applies a correction in a part of the preset operation mode to operate the robot main body 1.

In this embodiment, the operation of the slave arm 10 in the correctable automatic mode is controlled by correcting target angular positions of the plurality of joint axes of the preset operation mode stored in the memory part 32 based on angular positions of the corresponding joint axes received from the master arm 70, and by controlling with the motion controlling module 33 the robotic arm drive part of the arm main body 13 to bring the angular positions of the plurality of joint axes of the slave arm 10 to the respective corrected target angular positions. Thus, the slave arm 10 is configured to operate upon the correction by the motion of the master arm 70.

The operational instruction content identifying module 34, based on operational instruction content data stored in the memory part 32, identifies one hand gesture detected by the contactless action detecting part 71, that is, the operation mode of the robot main body 1 corresponding to the operation instructing action.

In addition, the controller 31 is configured to process information of an image captured by the camera 51 and then output it to the monitor 52. Thus, the operator can control the master arm 70 while checking the work situation of the slave arm 10 displayed on the monitor 52. Note that the camera 51 and the monitor 52 may be connected directly to each other without going through the control device 3.

FIG. 4 is a view illustrating a configuration example of the operational instruction content data stored in the memory part 32. FIGS. 5A to 5E are flowcharts illustrating configuration examples of the operation mode of the robot main body 1.

The memory part 32 has memories, such as a ROM and a RAM. The memory part 32 stores given programs and the controller 31 reads and executes these control programs to control the operation of the robot main body 1. Further, as illustrated in FIG. 4 and FIGS. 5A to 5E, the memory part 32 stores operational instruction content data which defines the operation mode of the robot main body 1 corresponding to each of one or more operation instructing actions (hand gestures).

That is, in this embodiment, the memory part 32 stores the operational instruction content data, including the data which defines operation modes related to "hold workpiece," "reference attitude," "advance," "release workpiece," and "retreat" which are associated with given hand gestures.

Figure 5A:
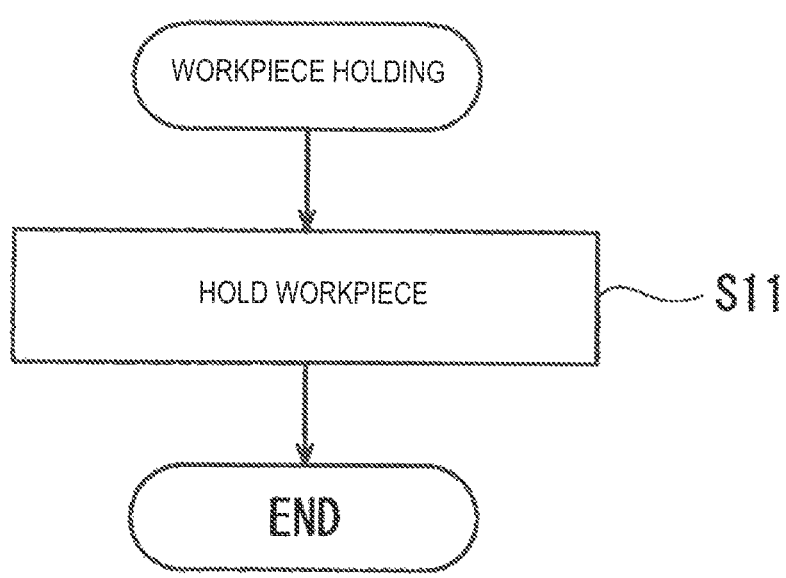
FIG. 5A is a flowchart illustrating a configuration example of an operation mode of the remote control robot system in FIG. 1.

As illustrated in FIG. 4, a first hand gesture in which fingers are bent as if grabbing an object with the palm facing down is associated with the operation mode related to "hold workpiece." As illustrated in FIG. 5A, the operation mode related to "hold workpiece" is a mode in which the robot main body 1 is operated according to an operation mode in which a holding operation of the workpiece is performed by the end effector 16 (Step S11).

Figure 5B:
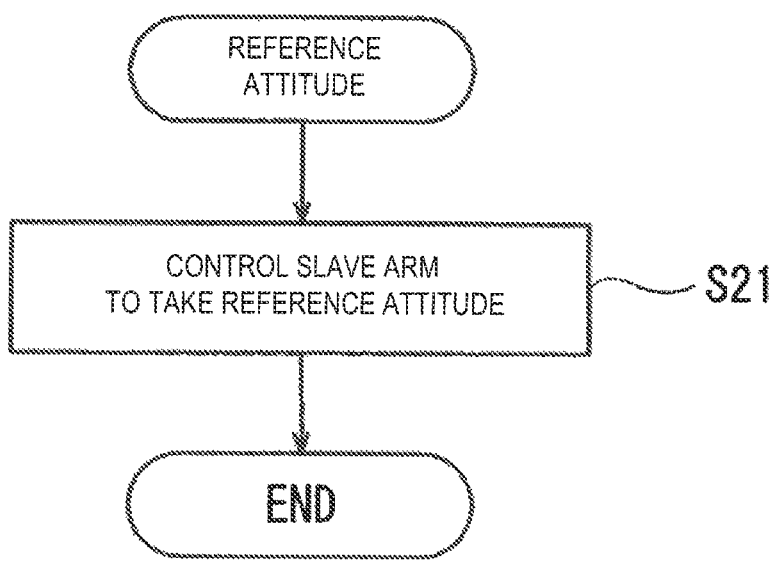
FIG. 5B is a flowchart illustrating a configuration example of an operation mode of the remote control robot system in FIG. 1.

Further as illustrated in FIG. 4, a second hand gesture in which the hand is closed with the back of the hand facing up is associated with the operation mode related to the "reference attitude." As illustrated in FIG. 5B, the operation mode related to "reference attitude" is a mode in which the robot main body 1 is operated according to an operation mode in which the slave arm 10 takes a given reference attitude (Step S21). In this embodiment, the given reference attitude is an attitude in which a workpiece W which is held by the end effector 16 is located at a position suitable for transporting the workpiece W.

Figure 5C:
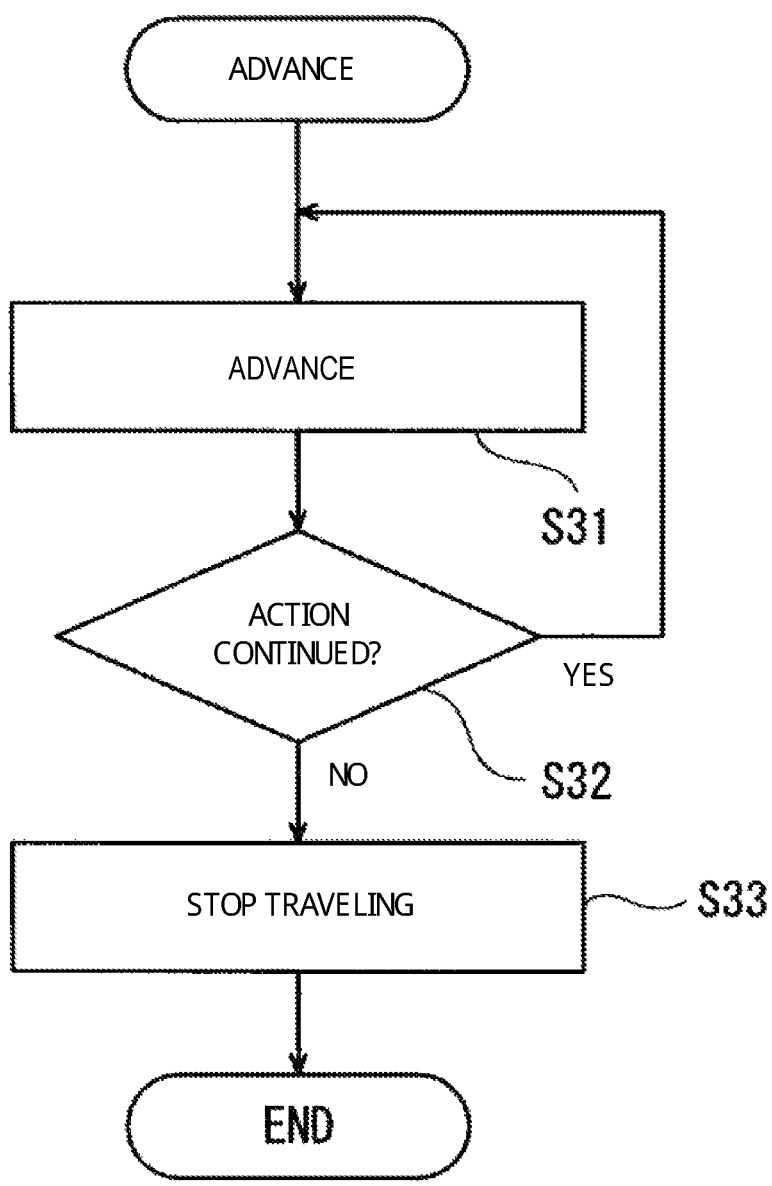
FIG. 5C is a flowchart illustrating a configuration example of an operation mode of the remote control robot system in FIG. 1.

Further, as illustrated in FIG. 4, a third hand gesture in which finger tips other than a thumb are bent and stretched with the palm facing up is associated with the operation mode related to "advance." As illustrated in FIG. 5C, the operation mode related to "advance" is a mode in which the robot main body 1 is operated according to an operation mode in which the robot main body 1 is advanced (Step S31), then is kept advancing while the operator is making the third hand gesture (YES at Step S32), and once the operator stops making the third hand gesture (NO at Step S32), the traveling of the robot main body 1 is stopped (Step S33).

Figure 5D:
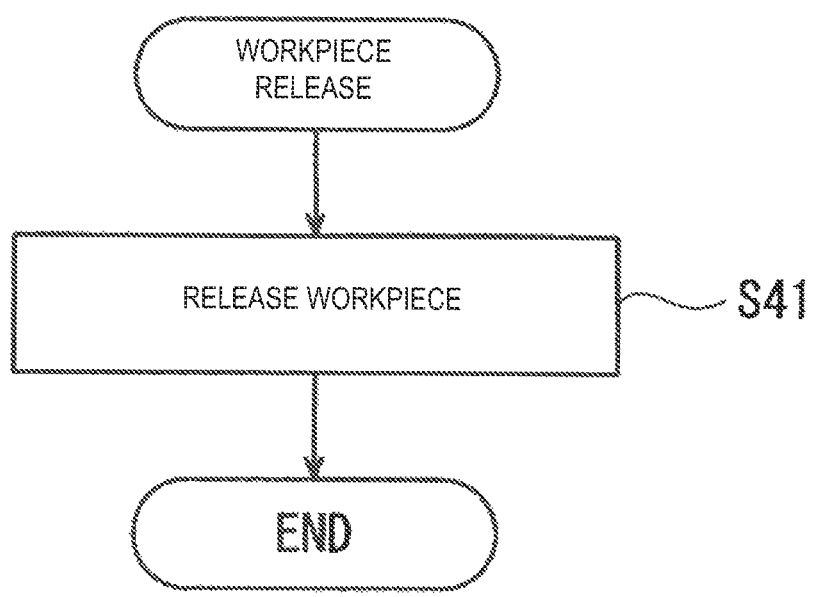
FIG. 5D is a flowchart illustrating a configuration example of an operation mode of the remote control robot system in FIG. 1.

Further, as illustrated in FIG. 4, a fourth hand gesture in which fingers are stretched with the palm facing down is associated with the operation mode related to "release workpiece." As illustrated in FIG. 5D, the operation mode related to "release workpiece" is a mode in which the robot main body 1 is operated according to an operation mode in which a releasing operation of the workpiece W is performed by the end effector 16 (Step S41).

Figure 5E:
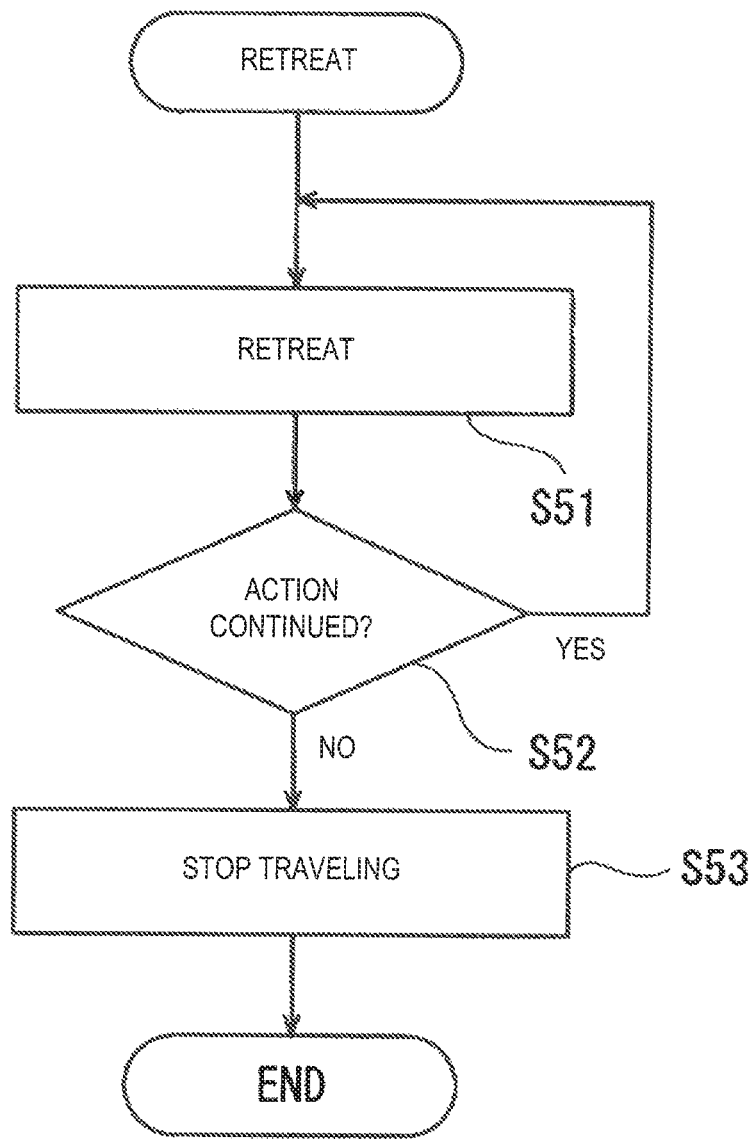
FIG. 5E is a flowchart illustrating a configuration example of an operation mode of the remote control robot system in FIG. 1.

Further, as illustrated in FIG. 4, a fifth hand gesture in which the finger tips other than the thumb are bent and extended with the palm facing down is associated with the operation mode related to "retreat." As illustrated in FIG. 5E, the operation mode related to "retreat" is a mode in which the robot main body 1 is operated according to an operation mode in which the robot main body 1 is retreated (Step S51), then is kept retreating while the operator is making the fifth hand gesture (YES at Step S52), and once the operator stops making the fifth hand gesture (NO at Step S52), the traveling of the robot main body 1 is stopped (Step S53).

The first to fifth hand gestures are not limited to the modes described above but a hand gesture matching an operator's impression on the operational instruction content may be selected and set as an operation instructing action. Thus, a required period of time for the operator to memorize the correspondence between the operational instruction and the hand gesture (operation instructing action) and be familiar with the method of operating the remote control robot system 100 can be shortened.

Further, since it is possible to input the operational instruction to the contactless action detecting part 71 without touching, there is no need to visually recognize the contactless action detecting part 71 at the time of inputting an operational instruction to the contactless action detecting part 71, and it is possible to, for example, input an operational instruction to the contactless action detecting part 71 while keeping the focus on the monitor 52. Therefore, it is possible to promptly input the operational instruction, and it is possible to prevent the work from being interrupted due to moving his/her eyes away from the monitor 52.

Furthermore, it is possible that hand gestures which are clearly distinguishable from each other as the respective hand gestures are selected and set as the operation instructing actions, preventing incorrect input and erroneous recognition by the operator.

Note that in this embodiment, the first to fifth hand gestures are all inputted by one of the operator's hands. Thus, it is possible to make a hand gesture with one hand to input the operational instruction for the robot main body 1 to the remote control robot system 100, while simultaneously controlling the master arm 70 with the other hand to input the operational instruction for the slave arm 10 to the remote control robot system 100. As a result, a plurality of operational instructions are able to be inputted simultaneously.

The signals outputted from the master arm 70, the contactless action detecting part 71, and the mode selecting part 75 of the remote control device 2 are inputted to the control device 3. Further, the signal outputted from the camera 51 is inputted to the control device 3.

It is configured such that the communication between the remote control device 2 and the control device 3 and the communication between the control device 3 and the robot main body 1 are performed by a manner of using wire or wirelessly as appropriate.

Operation Example

Next, an operation example of the remote control robot system 100 will be described.

This operation example is an operation example in a case where the workpiece W stored in a workpiece storage is installed at an installation position P (see FIG. 1).

First, in a state where the manual mode is selected at the mode selecting part 75 and the robot main body 1 is located in the workpiece storage, the operator controls the master arm 70 to operate the slave arm 10 so as to place the end effector 16 at a position where the end effector 16 can hold the workpiece W.

Next, when the operator makes the first hand gesture which includes the hand shape like grabbing an object, the contactless action detecting part 71 detects the first hand gesture, and the attitudes of the respective fingers and the hand motion related to the first hand gesture are transmitted to the control device 3. Then, the operational instruction content identifying module 34 determines that the operational instruction related to the operation mode of "hold workpiece" has been inputted to the remote control robot system 100 based on the first hand gesture. Then, the motion controlling module 33 controls the end effector 16 to perform the holding operation of the workpiece (Step S11).

Next, when the operator makes the second hand gesture, the operational instruction content identifying module 34 determines that the operational instruction related to the operation mode of "reference attitude" has been inputted to the remote control robot system 100 based on the second hand gesture. Then, the motion controlling module 33 controls the slave arm 10 to take the reference attitude (Step S21). Thus, the workpiece W is located at a position suitable for transportation.

Next, when the operator makes the third hand gesture which includes the hand shape and motion like beckoning, the operational instruction content identifying module 34 determines that the operational instruction related to the operation mode of "advance" has been inputted to the remote control robot system 100 based on the third hand gesture. Then, the motion controlling module 33 controls the traveling unit 17 to cause the robot main body 1 to advance (Step S31), and then cause the robot main body 1 to keep advancing while the third hand gesture is continuously made (YES at Step S32). Then, when the robot main body 1 arrives near the installation position P and the operator stops making the third hand gesture (NO at Step S32), the motion controlling module 33 controls the traveling unit 17 to stop the robot main body 1 (Step S33).

Next, the operator controls the master arm 70 to operate the slave arm 10 to locate the workpiece W, which is held by the end effector 16, at the installation position P. Then, when the operator makes the fourth hand gesture which includes the hand shape like releasing the object, the operational instruction content identifying module 34 determines that the operational instruction related to the operation mode of "release workpiece" has been inputted to the remote control robot system 100 based on the fourth hand gesture. Then, the motion controlling module 33 controls the end effector 16 to perform the releasing operation of the workpiece (Step S41).

Next, when the operator makes the fifth hand gesture which includes the hand shape and motion like rejecting, the operational instruction content identifying module 34 determines that the operational instruction related to the operation mode of "retreat" has been inputted to the remote control robot system 100 based on the fifth hand gesture. Then, the motion controlling module 33 controls the traveling unit 17 to cause the robot main body 1 to retreat (Step S51), and then cause the robot main body 1 to keep retreating while the fifth hand gesture is continuously made (YES at Step S52). Then, when the operator stops making the fifth hand gesture (NO at Step S52), the motion controlling module 33 controls the traveling unit 17 to stop the robot main body 1 (Step S53).

As described above, in the remote control robot system 100 according to the present disclosure, the operator can select and set the action matching the impression on the operational instruction content as the operation instructing action and, by using the set operation instructing action, input the operational instruction corresponding to this operation instructing action, to the remote control robot system 100. Thus, a required period of time for the operator to memorize the correspondence between the operational instruction and the hand gesture (operation instructing action) and be familiar with the method of manipulating the remote control robot system 100 can be shortened.

Further, since it is possible to input the operational instruction to the contactless action detecting part 71 without touching, there is no need to visually recognize the contactless action detecting part 71 at the time of inputting an operational instruction to the contactless action detecting part 71, and it is possible to, for example, input an operational instruction to the contactless action detecting part 71 while keeping the focus on the monitor 52. Therefore, it is possible to promptly input the operational instruction, and it is possible to prevent the work from being interrupted by moving his/her eyes away from the monitor 52.

Furthermore, it is possible that actions which are clearly distinguishable from each other as the respective operation instructing actions are selected and set as the operation instructing actions, preventing incorrect input and erroneous recognition by the operator.

Second Embodiment

Hereinafter, configurations and operations of the second embodiment will be described focusing on differences from the first embodiment.

FIG. 6 is a view illustrating a configuration example of operational instruction content data according to this embodiment, which is stored in the memory part 32.

In the first embodiment, the operation instructing action is the operator's hand gesture and the contactless action detecting part 71 is the detector for detecting the operator's hand gesture. Meanwhile in this embodiment, the operation instructing action is operator's sound of voice, and the contactless action detecting part is a detector for detecting the sound, for example, a microphone.

Further, in the first embodiment, the memory part 32 stores the operational instruction content data which contains the definition of the operation modes related to "hold workpiece," "reference attitude," "advance," "release workpiece," and "retreat" which are associated with the given hand gestures. Meanwhile in this embodiment, the memory part 32 stores the operational instruction content data which contains the definition of the operation modes related to "hold workpiece," "reference attitude," "advance," "release workpiece," and "retreat" which are associated with given sounds.

As illustrated in FIG. 6, the operation mode related to "hold workpiece" is associated with a first sound related to a sound of voice "hold workpiece." Further, the operation mode related to "reference attitude" is associated with a second sound related to a sound of voice "take reference attitude." Further, the operation mode related to "advance" is associated with a third sound related to a sound of voice "advance." Further, the operation mode related to "release workpiece" is associated with a fourth sound related to a sound of voice "release workpiece." Moreover, the operation mode related to "retreat" is associated with a fifth sound related to a sound of voice "retreat." Note that, the operation modes related to "hold workpiece," "reference attitude," "advance," "release workpiece," and "retreat" are the similar as those in the first embodiment.

As described above, in this embodiment, by inputting the first to fifth sounds to the contactless action detecting part 71, the motion controlling module 33 operates the robot main body 1 according to the corresponding operation modes.

Third Embodiment

In the first embodiment, the contactless action detecting part 71 for detecting the operator's hand gesture includes the infrared radiator 71a, and the stereo camera 71b for receiving the infrared ray radiated from the infrared radiator 71a and reflected on the target object. Meanwhile in this embodiment, the contactless action detecting part 71 for detecting the operator's hand gesture is a glove to be worn on the operator's hand, and includes a sensor for detecting the attitude of each finger and the motion of the hand.

Fourth Embodiment

In the first embodiment, the control device 3 operates the robot main body 1 in accordance with the operational instruction inputted via the contactless action detecting part 71 in the manual mode, but without limiting to this, it may be operated in the correctable automatic mode.
<Modifications>

In the above embodiments, the master arm 70 is a device by which the target attitude of the slave arm 10 can be inputted, but it is not limited to this. Alternatively to this, the master arm may be a device by which a target position and target attitude of the end effector 16 are inputted. Further, in the manual mode, the motion controlling module 33 may calculate the attitude of the slave arm 10 at which the end effecter takes the detected target position and target attitude, and control the operation of the slave arm 10 so that the slave arm 10 takes the attitude.

From the above description, many improvements and other embodiments of the present disclosure are apparent for a person skilled in the art. Therefore, the above description is to be interpreted only as illustration, and it is provided in order to teach a person skilled in the art the best mode in which the present disclosure is implemented. Details of the structures and/or functions of the present disclosure may be substantially changed without departing from the spirit of the present disclosure.

DESCRIPTION OF REFERENCE CHARACTERS

1 Robot Main Body
2 Remote Control Device
3 Control Device
10 Slave Arm
13 Arm Main Body
15 Pedestal
16 End Effector
17 Traveling Unit
31 Controller
32 Memory Part
33 Motion Controlling Module
34 Operational Instruction Content Identifying Module
51 Camera
52 Monitor
70 Master Arm
71 Contactless Action Detecting Part
75 Mode Selecting Part
100 Remote Control Robot System

The invention claimed is:

1. A remote control robot system, comprising:
a robot main body having a slave arm;
a remote control device including:
    a master arm for an operator to control by touching, to input an operational instruction for the slave arm; and
    a contactless action detecting part configured to detect a contactless action including at least one operation instructing action of the operator; and
a control device communicably connected to the remote control device and configured to control operation of the robot main body, the control device including:
    a memory part configured to store operational instruction content data defining an operation mode of the robot main body corresponding to the at least one operation instructing action;
    an operational instruction content identifying module configured to identify the operation mode of the robot main body corresponding to one of the operation instructing action detected by the contactless action detecting part based on the operational instruction content data; and
    a motion controlling module configured to control operation of the robot main body based on the operation mode identified by the operational instruction content identifying module.

2. The remote control robot system of claim 1, wherein the operation instructing action is an operator's hand gesture.

3. The remote control robot system of claim 2, wherein the hand gesture is inputted by one of operator's hands.

4. The remote control robot system of claim 1, wherein the operation instructing action is operator's sound of voice.

5. The remote control robot system of claim 1,
wherein the slave arm has an arm that is attachable, at its tip-end part, to an end effector configured to handle a workpiece, and that is configured to move the end effector within a given operational area by moving the tip-end part with respect to a base-end part, and
wherein the operation mode of the robot main body in the operational instruction content data includes an operation mode in which the end effector is operated.

6. The remote control robot system of claim 1,
wherein the robot main body includes a traveling unit configured to cause the robot main body to travel, and
wherein the operation mode of the robot main body defined by the operational instruction content data includes an operation mode in which the robot main body travels by the traveling unit.

* * * * *